United States Patent [19]

Traas et al.

[11] Patent Number: 4,719,040
[45] Date of Patent: Jan. 12, 1988

[54] PROCESS FOR THE PREPARATION OF AIR-FRESHENER GELS

[75] Inventors: Petrus C. Traas; Ernst-Ludwig Roehl, both of Naarden, Netherlands

[73] Assignee: Naarden International N.V., Naarden-Bussum, Netherlands

[21] Appl. No.: 700,763

[22] Filed: Feb. 12, 1985

[30] Foreign Application Priority Data

Feb. 17, 1984 [NL] Netherlands .......................... 8400516

[51] Int. Cl.⁴ .............................. A61K 7/46; C11B 9/00
[52] U.S. Cl. ........................................................ 512/4
[58] Field of Search ...................................... 252/522 A

[56]  References Cited
U.S. PATENT DOCUMENTS 3,446,893  5/1969  Hanford et al. .
3,745,213  7/1973  Nysted .
3,994,439  11/1976  Van Breen et al. ........ 252/522 A X
4,351,754  9/1982  Dupre .

FOREIGN PATENT DOCUMENTS 0061701  10/1982  European Pat. Off. .
0038436   3/1976  Japan ............................ 252/522 A
0055740   4/1979  Japan ............................ 252/522 A
0055372   1/1981  Japan ............................ 252/522 A
1576228  10/1980  United Kingdom .

Primary Examiner—Helen M. S. Sneed
Attorney, Agent, or Firm—Brumbaugh, Graves, Donohue & Raymond

[57]  ABSTRACT

Process for the preparation of aqueous air freshener gels having an increased perfume content of at least 5% and preferably more than 10% of the total weight of the gel by taking up the perfume in finely divided, porous, water-insoluble, synthetic polymer as the carrier and subsequently combining the thus obtained perfume-laden carrier with an aqueous gel or with the gelforming components.

12 Claims, No Drawings

PROCESS FOR THE PREPARATION OF AIR-FRESHENER GELS

The invention relates to a process for the preparation of air-freshener gels and to the gels thus obtained.

Air-freshener gels are popular consumer products. They consist of a perfume-containing carrier material, from which the perfume slowly evaporates and thus imparts a pleasant odour to the atmosphere. The working life and the quantity of perfume released per unit time are, to a considerable extent, determined by the amount of perfume which an air freshener contains. In many known types of air fresheners gelled water is used as the carrier material. Since perfumes are generally insoluble or sparingly soluble in water, they must be dispersed therein, as homogeneously as possible. Gelled organic solvents such as monohydric or polyhydric alcohols or glycol-ethers are also used as the carrier material. However, water has the advantage that it is a cheap and toxicologically safe base material.

Aqueous gels can be prepared in numerous ways known per se, and as gelling agents there may be used vegetable and microbial gums such as carragheen, agar agar, alginates, pectins, guar gum, tragacanth, karaya gum, xanthan and the like, and also, for example, gelatine, starch derivatives and cellulose derivatives. In some cases the gel strength can be increased by adding salts of divalent or polyvalent metals such as Ca, Mg, Al or Cr. Synthetic polymers such as polyvinyl alcohol can also be used as the gelling agent.

Such aqueous gels have the disadvantage that they can only contain a limited amount of perfume. Mostly, a maximum perfume content of about 10% is given in the literature, but in practice it appears that at a perfume content above about 6% the gel strength greatly decreases and/or syneresis occurs, with the perfume exuding as a liquid from the gel. Aqueous perfume gels are described, for example, in Japanese Published Patent Applications Nos. 54/110,990 (gelling agent: carragheen and sodium stearate, perfume content up to 6%); 53/088,334 (gelling agent: bacterial polysaccharide, 1-10% of perfume) and 52/136,893 (gelling agent: carragheen and polyvinyl alcohol, 2-4% of perfume), and in French Patent Application No. 2,293,976 (gelling agent: carboxymethylcellulose/Al salt, 5% of perfume).

Netherlands Patent Application No. 76/11041 also describes the use of carboxymethylcellulose and salts of trivalent metals as gelling agents in aqueous perfume gels. Though the description reports that these gels can contain up to 20% of perfume, the examples only show a perfume content of 4%. Equally, Netherlands Patent Application No. 76/02254 describes similar aqueous perfume gels which are supposed to be able to contain up to 10% of perfume, while the examples only range up to 2.5% of perfume. Netherlands Patent Application No. 75/02596 describes aqueous gels based on mixtures of carragheen and locust bean flour, which according to the description can also contain up to 10% of perfume, but here again the examples do not reveal more than 3.3% of perfume being used.

Netherlands Patent Application No. 76/12909 describes gels based on amylose as the gelling agent. The description states that the perfume content of these gels is 0.25-30%, but preferably 0.5-5%.

One of the examples does indeed report a gel with 30% of perfume, but for this a content of 10% of pure (and thus expensive) amylose is needed. When starch containing 70% of amylose is used, a stable gel can no longer be produced even at 10% of perfume. Moreover, these gels have the disadvantage that for the preparation of the requisite amylose solution high temperatures (up to 170° C.) and pressures (up to 7 atmospheres), and therefore relatively complicated apparatus, are needed.

A few of the abovementioned patent applications report that it is advisable to add a quantity of emulsifier to the perfume in order to assist homogeneous distribution of the perfume in the aqueous phase. Japanese Patent Application No. 52/070,035 reports that aqueous gels cannot contain more than 2-3% of perfume unless a nonionic emulsifier is added in an amount which is 0.5-1.5 times the amount of perfume, in which case the perfume content of the gel can be as high as 10%. Moreover, it is true in all cases that the amount of perfume which can be mixed homogeneously into an aqueous gel depends to a considerable extent on the degree of solubility of the perfume in water and hence on the nature of the constituent components of the perfume.

The term "perfume" here means a mixture of organic compounds, such as aldehydes, ketones, nitriles, esters, carboxylic acids, alcohols, ethers and the like, which can also contain products of natural origin, such as ethereal oils, resin oils, balsams, concretes and the like. This mixture is intended to spread a desired odour. In many cases a perfume contains a—generally small—quantity of a solvent or diluent customary in perfumery, for example because one or more of the components used for the composition is only supplied in solution or can only be handled in solution.

It is the object of the invention to provide aqueous air freshener gels which have an increased perfume content and hence a longer working life and/or a higher perfume release per unit time. By "increased perfume content" there is meant, in the present context, a content of at least 5% and preferably of more than 10% of the total weight of the gel.

It has now been found that such gels can be prepared by first taking up the perfume in a finely divided, porous, water-insoluble, synthetic polymer as the carrier material and thereafter incorporating this mixture of carrier material and perfume, which hereinafter will be referred to as "premix", in an aqueous gel. Preferably, a pulverulent, porous, water-insoluble synthetic polymer is used as the carrier material.

As the carrier materials, it is possible to use any synthetic polymer which has an open-pore structure and can hold a perfume in its pores. Since perfumes in general have a predominantly hydrophobic character, the polymer should also preferably have a predominantly hydrophobic character. The polymers used can be addition polymers, for example of the polyalene type, condensation polymers or oxidation polymers. In the case of some types of polymers, the perfume is preferably added, before or during the polymerisation, to the polymer base material, whether it be a monomer or a mixture of one or more monomers and/or one or more so-called prepolymers. The pores of the polymer thus formed are at the same time filled with the perfume. In the case of other types of porous polymers or of processes for the preparation thereof, a porour polymer structure is obtained, the pores of which can afterwards be filled with perfume, for example by simple mixing, where appropriate under vacuum.

Suitable polymers, processes for the preparation thereof and processes for taking up the perfume in the polymer matrix are described, for example, in British Patent Specification No. 1,576,228, in European Patent Application No. 61,701 and in the literature cited in these publications.

The aqueous gels according to the invention can be prepared by using gelling agents which are known and are customary for aqueous gels, such as the gelling agents described, for example, in the patents and patent applications already mentioned, and in the literature cited therein. Very suitable gelling agents are, for example, agar agar, carragheen and modified cellulose such as methylcellulose, hydroxyethylcellulose and carboxymethylcellulose. Some gelling agents can advantageously be combined with a salt of a polyvalent metal as a crosslinking agent. A part of the water to be used for the gel can, if desired, be replaced by water-miscible organic solvents, in particular monohydric or polyhydric alcohols such as ethanol, isopropanol, ethylene glycol and the like, to the extent that these do not detract from the satisfactory action of the gelling agent used. In general, this replacement is however inadvisable, for economic reasons, since organic solvents are more expensive than water.

The amount of perfume present in a gel according to the invention is determined by, on the one hand, the amount of perfume in the premix and, on the other hand, the amount of premix in the gel. This last amount is not subject to any basic restriction but is in practice limited by the fact that in the preparation of the gel mixture the viscosity increases with increasing amount of premix.

The maximum amount of premix to be used is therefore determined by the requirements as to the processability of the gel mixture during preparation, and by the apparatus which is available for the preparation. If it is required that immediately after preparation the mixture should be so liquid that it can easily be poured into moulds, a maximum of about 35% of premix can be incorporated into a gel. If, however, use is made, in the preparation, of heavy-duty stirrers, and the gel package is filled by means of apparatus which works under pressure, then substantially higher premix contents are achievable.

The maximum perfume content of the premix is determined by the requirement that the premix must be solid, though it is no disadvantage if the premix is somewhat damp or lumpy. The minimum amount of polymeric carrier needed to meet this requirement depends on the type of polymer and on its degree of porosity.

In the case of the customary polymeric carriers such as those described, for example, in the above-mentioned British Patent Specification No. 1,576,228 and European Patent Application No. 61,701, the premix can in most cases readily contain 75–90% of perfume. In the case of some carriers, even perfume contents of 90–95% in the premix are possible.

In some cases, especially when the premix contains so much perfume that it is damp, it can be advisable to add a small amount of emulsifier in the preparation of the gel, in orer to assist homogeneous distribution of the premix in the gel mixture. Preferably, emulsifiers having an HLB value of 9 or more are used for this purpose, such as fatty acid esters of polyethylene glycols, and condensation products of alkylphenols or fatty alcohols with ethylene oxide.

A gel to be prepared with simple means and containing at most 35% of premix will therefore, taking account of the abovementioned provisos, in general have a composition which conforms to the following table:

|  |  | preferably |
|---|---|---|
| porous polymeric carrier | 0.1–30% | 1–25% |
| perfume | 5–33% | 10–31% |
| emulsifier | 0–5% |  |
| water (if desired, partially a water-miscible organic solvent) | 45–94.4% | max. 88.5% |
| gelling agent | 0.5–10% |  |
| polyvalent metal salt | 0–5% |  |
| preservative | 0–1% |  |
| colourant | 0–0.1% |  |

The preparation of the gel is carried out in accordance with methods known per se for such products, except that, according to the invention and differing from these methods, the perfume is beforehand taken up in the polymeric carrier material, giving a homogeneous mixture, here referred to as the premix. Such premixes are also available commerically in a ready-to-use form. The premix, where appropriate after mixing with a desired amount of emulsifier, is mixed with water, gelling agent and, where appropriate, metal salt, preservative and colourant. Preferably, the water, gelling agent and other constituents, except for the premix and, where appropriate, the emulsifier, are mixed beforehand, and the premix is then added as quickly as possible thereafter. Many gel mixtures are preferably prepared at an elevated temperature and subsequently poured into moulds at this temperature.

On cooling to room temperature, the gel mixture solidifies. However, gel types are also known which can be prepared at room temperature and remain liquid for a sufficiently long time that they can be poured into moulds. All these and similar methods can be used for the preparation of the gels according to the invention.

An example of a perfume which can be used in the gels according to the invention was prepared in accordance with the following recipe:

| | |
|---|---|
| 300 | parts by weight of bornyl acetate |
| 200 | parts by weight of Florida orange oil |
| 140 | parts by weight of β-phenylethanol |
| 100 | parts by weight of geraniol |
| 100 | parts by weight of α-pentyl-cinnamaldehyde |
| 75 | parts by weight of benzyl acetate |
| 50 | parts by weight of dihydromyrcenol |
| 30 | parts by weight of 2,4-dimethyl-3-cyclohexene-carbaldehyde |
| 5 | parts by weight of decanal |
| 1000 | parts by weight |

The examples are intended solely to illustrate the process according to the invention and the invention is in no way restricted thereto.

EXAMPLE I 5 g of Accurel (a trademark for porous polymer powders of Enka AG, Obernburg, Federal Republic of Germany) polypropylene powder (75% void space) were laden with 25 g of the abovementioned perfume by mixing the two components in vacuo. This gave a somewhat damp powder which was subsequently mixed with 4.5 g of water. 2.5 g of carragheen, 0.3 g of chloroacetamide and 0.5 g of $CaCl_2 \cdot 2H_2O$ were dissolved in 62.2 g of water, with warming to about 75° C. The premix described above was added to this somewhat viscous solution and the mixture was stirred thoroughly until a homogeneous mixture was obtained. This was filled into moulds while warm. On cooling to room temperature, stiff and stable air freshner gels having a perfume content of 25% were obtained.

EXAMPLE II

A mixture of 2.2 g of Gelcarin AFG 75 (a trademark for carragheen of Marine Colloids Inc., Springfield, N.J., USA) and 0.4 g of Methocel E 50 (a trademark for methylcellulose of Dow Chemical USA, Midland, Mich., USA) was added, with good stirring, to a solution of 0.1 g of methylparabene in 66.3 g of water. The whole mixture was warmed to 80° C., while stirring.

28.6 g of Polytrap (a trademark for porous polymer powder laden with perfume, of Wickhen Products Inc., Big Pond Road, Huguenot, N.Y., USA) polymer powder having a perfume content of 70% by weight were mixed with 2.4 g of Arlypon NP-14 (a trademark for a nonionic emulsifier of Chemische Werke Grünau, Illertissen, Federal Republic of Germany). The hot Gelcarin solution was added to the polymer powder and the whole was stirred thoroughly until a homogeneous mixture was obtained, which was subsequently poured into moulds while warm. On cooling to room temperature, stiff and stable gels having a perfume content of 20% were obtained.

We claim:

1. Process for the preparation of aqueous air freshener gels comprising the steps of:
   preparing a premix comprising at least 5% by weight of a finely divided porous water-insoluble synthetic polymer and at most 95% by weight of a perfume;
   preparing a mixture comprising at least 5.1% by weight of this premix and aqueous gel-forming components comprising at least 0.5% by weight of a gelling agent and at most 94.4% by weight of water; and preparing a gel from the mixture.

2. Process according to claim 1 wherein the premix is prepared by mixing the perfume with the polymer components before or during polymerization.

3. Process according to claim 1 wherein the premix is prepared by mixing the perfume with a finely divided open-pore porous polymer.

4. Process according to claim 1 wherein the gel-forming components are first mixed and the premix is added thereafter.

5. Process according to claim 1 wherein the premix comprises at least 10% by weight of polymer and at most 90% by weight of perfume.

6. Process according to claim 1 wherein at most 5% by weight of an emulsifier is added together with the premix.

7. Process for the preparation of aqueous air freshener gels comprising the steps of:
   preparing a premix comprising at least 10% by weight of a finely divided porous water-insoluble synthetic polymer and at most 90% by weight of a perfume;
   preparing a mixture comprising:
   5.1-35% by weight of the premix,
   0-5% by weight of an emulsifier
   45-94.4% by weight of water,
   0.5-10% by weight of gelling agent
   0-5% by weight of polyvalent metal salt,
   0-1% by weight of preservative,
   0-0.1% by weight of colorant; and preparing a gel from the mixture.

8. Process according to claim 7 wherein the premix is prepared by mixing the perfume with the polymer components before or during polymerization.

9. Process according to claim 7 wherein the premix is prepared by mixing the perfume with a finely divided open-pore porous polymer.

10. Process according to claim 7 wherein the gel-forming components are first mixed and the premix is added thereafter.

11. Aqueous air freshener gels comprising at least 5.1% by weight of the total gel of a premix prepared from at least 0.5 part by weight of a finely divided porous water-insoluble synthetic polymer and at most 9.5 parts by weight of a perfume, which premix is intimately mixed with aqueous gel-forming components comprising at least 0.5% by weight of a gelling agent and at most 94.4% by weight of water.

12. Aqueous air freshener gels comprising 5.1-35% by weight of the total gel of a premix prepared from at least 1 part by weight of a finely divided porous water-insoluble synthetic polymer and at most 9 parts by weight of a perfume, which premix is intimately mixed with aqueous gel-forming an auxiliary components comprising:
   0-5% by weight of an emulsifier
   45-94.4% by weight of water,
   0.5-10% by weight of gelling agent,
   0-5% by weight of polyvalent metal salt,
   0-1% by weight of preservative,
   0-0.1% by weight of colorant.

* * * * *